US008076453B2

(12) United States Patent
Gobeil, Jr. et al.

(10) Patent No.: US 8,076,453 B2
(45) Date of Patent: Dec. 13, 2011

(54) KININ $B_1$ RECEPTOR PEPTIDE AGONISTS AND USES THEREOF

(75) Inventors: Fernand Gobeil, Jr., Sherbrooke (CA); Witold A. Neugebauer, Ottawa (CA); Domenico Regoli, Sherbrooke (CA); David Fortin, Sherbrooke (CA)

(73) Assignee: Societe De Commercialisation Des Produits De La Recheche Appliquee-Socpra-Science Sante Et Humaines S.E.C., Sherbrooke (CA)

( * ) Notice: Subject to any disclaimer, the term of this patent is extended or adjusted under 35 U.S.C. 154(b) by 289 days.

(21) Appl. No.: 11/916,136

(22) PCT Filed: May 31, 2006

(86) PCT No.: PCT/CA2006/000890
§ 371 (c)(1),
(2), (4) Date: Aug. 8, 2008

(87) PCT Pub. No.: WO2006/128293
PCT Pub. Date: Dec. 7, 2006

(65) Prior Publication Data
US 2009/0054347 A1 Feb. 26, 2009

(51) Int. Cl.
*C07K 7/00* (2006.01)
(52) U.S. Cl. ...................... 530/328; 514/21.6
(58) Field of Classification Search .................. 530/328; 514/21.6
See application file for complete search history.

(56) References Cited

U.S. PATENT DOCUMENTS

| | | | | |
|---|---|---|---|---|
| 5,541,286 A | * | 7/1996 | Kyle | 530/314 |
| 5,552,383 A | * | 9/1996 | Kyle et al. | 514/15 |
| 5,686,565 A | * | 11/1997 | Kyle et al. | 530/328 |
| 5,817,756 A | * | 10/1998 | Kyle et al. | 530/331 |

OTHER PUBLICATIONS

Rhaleb, N. et al., Structure-activity studies on bradykinin and related peptides: agonists, Br. J. Pharmacol, 1990, 445-448, 99.
Audet, R. et al., Cardiovascular Effects of Sar-[D-Phe8]des-Arg9-Bradykinin, a Metabolically Protected Agonist of B1 Receptor for Kinins, in the Anesthetized Rabbit Pretreated with a Sublethal Dose of Bacterial Lipopolysaccharide, J. Pharmacol Exp Ther, 1997, 6-15, 280-1.
Drapeau, G. et al. Hypothensive effects of Lys-des-Arg9-Bradykinin and metabolically protected agonists of B1 receptors for Kinins, J. Pharmacol Exp Ther, 1991, 997-1003, 259-3.
Nicolau, M. et al., Induction of bradykinin B1 hypotensive receptors in rats by lipopolysaccharide, Can. J. Physiol. Pharmacol., 1996, 337-340, 74.
Prat, A. et al., Kinin B1 receptor expression and function on human brain endothelial cells, J. Neuropathol Exp Neurol., 2000, 896-906, 59.
Cardoso, R.C. et al., Enhancement of blood-tumor barrier permeability by Sar-[D-Phe8]des-Arg9BK, a metabolically resistant bradykinin B1 agonist, in a rat C6 glioma model, BMC Neuroscience, 2004, 38-5.
Agata, J. et al., Bradykinin B1 Receptor Mediates Inhibition of Neointima Formation in Rat Artery After Balloon Angioplasty, Hypertension, 2000, 364-370, 36.
Black, K.L. et al., Biochemical opening of the blood-brain barrier, Adv. Drug Delivery Rev. 1995, 37-52, 15.
Bouchard J.F. et al., Role of kinins in the endothelial protective effect of ischaemic preconditioning, Brit J Pharmacology, 1998, 413-420, 123.
Chahine et al., Protective effects of bradykinin on the ischaemic heart: implication of the B1 receptor, Brit J Pharmacology, 1993, 318-322, 108.
Duguay D. et al., Kinin B2 receptor is not involved in enalapril-induced apoptosis and regression of hypertrophy in spontaneously hypertensive rat aorta: possible role of B1 receptor, Brit J Pharmacology, 2004, 728-736-322, 141.
Couture R. and Girolami J.P., Putative roles of kinin receptors in the therapeutic effects of angiotensin 1-converting enzyme inhibitors in diabetes mellitus, Eur. J. Pharmacol 2004, 467-485, 500(1-3).
Duka, I. et al. Vasoactive Potential of the B1 Bradykinin Receptor in Normotension and Hypertension, Circ. Res., 2001, 275-281, 88.
Duka A. et al. Role of bradykinin B1 and B2 receptors in normal blood pressure regulation, Am. J. Physiol Endocrinol. Metab., 2006, 268-274, 291.
Emmanueli, C., and Madeddu, P., Targeting kinin receptors for the treatment of tissue ischaemia, Trend in Pharmacol. Sci. 2001, 478-484, 22.
Emmanueli, C. et al., Targeting Kinin B1 Receptor for Therapeutic Neovascularization, Circulation. 2002, 360-366, 105.
Emerich, F.E. et al., Intravenous cereport (RMP-7) enhances delivery of hydrophilic chemotherapeutics and increases survival in rats with metastatic tumors in the brain, Pharm. Res., 2000, 1212-1219, 17.
Kichuck, M., Regulation of Nitric Oxide Production in Human Coronary Microvessels and the Contribution of Local Kinin Formation, Circulation, 1996, 44-51, 94.
Emerich, D.F., et al., Bradykinin Modulation of Tumor Vasculature: I. Activation of B2 Receptors Increases Delivery of Chemotherapeutic Agents into Solid Peripheral Tumors, Enhancing Their Efficacy, J Pharmacol Exp Ther, 2001, 623-631, 296.
Gobeil Jr, F. et al., Receptors for kinins in the human isolated umbilical vein, Brit. J. Pharmacol, 1996, 289-294, 118.
Gobeil Jr, F. et al. Characterization of non-peptide bradykinin B2 receptor agonist (FR 190997) and antagonist (FR 173657), Immunopharmacol, 1999, 179-185, 43.
Gobeil Jr, F. et al., Kinin B1 Receptor Antagonists Containing {alpha}-Methyl-L-Phenylalanine: In Vitro and In Vivo Antagonistic Activities, Hypertension, 1999, 823-829, 33.
Hagiwara, M. et al., Renal Protective Role of Bradykinin B1 Receptor in Stroke-Prone Spontaneously Hypertensive Rats,Hypertens. Res., 2004, 399-408, 27.

(Continued)

*Primary Examiner* — David Lukton
(74) *Attorney, Agent, or Firm* — Bereskin & Parr LLP/S.E.N.C.R.L., s.r.l.

(57) ABSTRACT

The present invention provides for novel kinin B1 receptors peptide agonists of formula (I) having very good to excellent affinities and selectivity for the $B_1$ receptor, in vitro and in vivo increased resistance to enzymatic degradation, superior pharmacokinetic properties to those of naturally occurring agents, capacity to significantly enhance delivery of chemotherapeutic substances across the blood brain barrier and within peripheral tissues for the treatment of tumors, capacity to protect and restore kidney, heart, brain and other organ functions, when given alone or in combination with other therapies in the treatment of hypertension, diabetes and other cardiovascular diseases particularly, but not limited to, atherosclerosis and arteriosclerosis. Formula (I): $aa^y\text{-}aa^x\text{-}aa^0\text{-}aa^1\text{-}aa^2\text{-}aa^3\text{-}aa^4\text{-}aa^5\text{-}Ser^6\text{-}Pro^7\text{-}D\text{-}Phe^8\text{-}X$.

18 Claims, No Drawings

OTHER PUBLICATIONS

Mathieu D. et al., The Importance of a Syngeneic Glioma Implantation Model: Comparison of the F98 Cell Line in Fischer and Long-Evans Rats, J. Appl. Res., 2005, 17-25, 5.

Parenti, A., et al. The bradykinin/B1 receptor promotes angiogenesis by up-regulation of endogenous FGF-2 in endothelium via the nitric oxide synthase pathway, FASEB J. 2001, 1487-1489, 15.

Sharma, J.N and Thani, R.B., Therapeutic prospects for bradykinin receptor agonists in the treatment of cardiovascular diseases, IDrug, 2004, 926-934, 7.

Tramontana, M. et al., Differences between Peptide and Nonpeptide B2 Bradykinin Receptor Antagonists in Blocking Bronchoconstriction and Hypotension Induced by Bradykinin in Anesthetized Guinea Pigs, J Pharmacol Exp Ther, 2001, 1051-1057, 296.

Xu, J. et al., Role of the B1 Kinin Receptor in the Regulation of Cardiac Function and Remodeling After Myocardial Infarction, Hypertension, 2005, 747-753, 45.

Rhaleb et al., 'Structure-activity studies on bradykinin and related peptides: Agonists' British Journal of Pharmacology vol. 99, 1990, pp. 445-448, XP008073361.

Audet et al.: 'Cardiovascular effects of Sar-[D-Phe8]des-Arg9-bradykinin, a metabolically protected agonist of B1 receptor for kinins, in the anesthetized rabbit pretreated with a sublethal dose of bacterial lipopolysaccharide' The Journal of Pharmacology and Experimental Therapeutics vol. 280, No. 1, 1997, pp. 6-15, XP003004845.

Drapeau et al.: 'Hypotensive effects of Lys-des-Arg9-bradykinin and metabolically protected agonists of B1 receptors for kinins' Journal of Pharmacology and Experimental Therapeutics vol. 259, No. 3, 1991, pp. 997-1003, XP008073351.

Nicolau et al.: 'Induction of bradykinin B1 hypotensive receptors in rats by lipopolysaccharide' Can. J. Physiol. Pharmacol. vol. 74, 1996, pp. 337-340, XP008073360.

Prat et al.: 'Kinin B1 receptor expression and function on human brain endothelial cells' Journal of Experimental Neurology vol. 59, No. 10, 2000, pp. 896-906, XP008073350.

Cardoso et al.: 'Enhancement of blood-tumor barrier permeability by Sar-[D-Phe8]desArg9BK, a metabolically resistant bradykinin B1 agonist, in a rat C6 glioma model' BMC Neuroscience vol. 5, No. 38, Sep. 30, 2004, p. 38, XP002102871.

Neugebauer W A et al: "Kinin B1 receptor antagonists with metabolic stability" Journal of Peptide Science, vol. 8, No. Supplement, 2002, p. S123, XP002557001 & 27th European Peptide Symposium; Sorrento, Italy; Aug. 31-Sep. 6, 2002 ISSN: 1075-2617.

Cote J et al: "Novel kinin B1 receptor agonists with improved pharmacological profiles" Peptides, Elsevier, Amsterdam, vol. 30, No. 4, Apr. 1, 2009, pp. 788-795, XP026070661 ISSN: 0196-9781 [retrieved on Dec. 27, 2008].

Xu J, Carretero OA, Sun Y, Shesely EG, Rhaleb NE, Liu YH, et al. Role of the B1 kinin receptor in the regulation of cardiac function and remodeling after myocardial infarction. Hypertension 2005;45:747-53.

Moniwa N, Agata J, Hagiwara M, Ura N, Shimamoto K. The role of bradykinin B1 receptor on cardiac remodeling in stroke-prone spontaneously hypertensive rats (SHR-SP). Biol Chem. 2006;387(2):203-9.

Tschope C, Spillmann F, Altmann C, Koch M, Westermann D, Dhayat N, et al. The bradykinin B1 receptor contributes to the cardioprotective effects of AT1 blockade after experimental myocardial infarction. Cardiovasc Res 2004;61:559-69.

Kakoki M, McGarrah RW, Kim HS, Smithies O. Bradykinin B1 and B2 receptors both have protective roles in renal ischemia/reperfusion injury. Proc Natl Acad Sci U S A 2007;104:7576-81.

Emanueli C, Bonaria Salis M, Stacca T, Pintus G, Kirchmair R, Isner JM, et al. Targeting kinin B(1) receptor for therapeutic neovascularization. Circulation 2002;105:360-6.

Emanueli C, Madeddu P. Targeting kinin receptors for the treatment of tissue ischaemia. Trends Pharmacol Sci 2001;22:478-84.

Chahine R, Adam A, Yamaguchi N, Gaspo R, Regoli D, Nadeau R. Protective effects of bradykinin on the ischaemic heart: implication of the B1 receptor. Br J Pharmacol 1993;108:318-22.

Griol-Charhbili V, Messadi-Laribi E, Bascands JL, Heudes D, Meneton P, Giudicelli JF, Alhenc-Gelas F, Richer C. Role of tissue kallikrein in the cardioprotective effects of ischemic and pharmacological preconditioning in myocardial ischemia. FASEB J. 2005 19(9):1172-4.

Agata J, Miao RQ, Yayama K, Chao L, Chao J. Bradykinin B(1) receptor mediates inhibition of neointima formation in rat artery after balloon angioplasty. Hypertension 2000;36:364-70.

Gobeil F, Côté J, Bélanger S, Tremblay L, Savard M, Lepage M, et al. Real-time monitoring of kinin B1 receptor-mediated selective blood brain tumour barrier opening using MRI. Kinin 2007, 2nd International Conference on exploring the future of vascular and inflammatory mediators; 2007; Berlin, Germany.

Côté, Jérôme et al., Selective tumor blood-brain barrier opening with the kinin B2 receptor agonist . . . in a F98 glioma rat model: An MRI Study, Neuropeptides 2010, 44: 177-185.

Côté, Jérôme et al., Novel kinin B1 receptor agonists with improved pharmacological profiles, Peptides 2009, 30: 788-795.

Couture, Réjean et al., Putative roles of kinin receptors in the therapeutic effects of angiotensin 1-converting enzyme inhibitors in diabetes mellitus, European Journal of Pharmacology 2004, 500: 467-485.

Bouchard, Jean-Francois et al., Role of kinins in the endothelial protective effect of ischaemic preconditioning, British Journal of Pharmacology 1998, 123: 413-420.

Pruneau D. et al., Induction of kinin B1 receptor-dependent vasoconstriction following balloon catheter injury to the rabbit carotid artery, Brit. J. Pharmacol, 1029-1034, 111.

* cited by examiner

KININ B₁ RECEPTOR PEPTIDE AGONISTS AND USES THEREOF

BACKGROUND OF THE INVENTION (a) Field of the Invention

The present invention relates to peptides derivatives of desArg$^9$-bradykinin (desArg$^9$-BK) which act as agonists at kinin $B_1$ receptors and their use as therapeutic agents.

(b) Description of Prior Art

Emerging findings suggest that the kallikrein-kinin system may play key position in blood pressure regulation and organ protection (Hagiwara et al., 2004, Hypertens Res 27(6), 399-408; Couture and Girolami, 2004, Eur J Pharmacol 500 (1-3), 467-485). Kinins are a group of bioactive peptides formed by numerous tissues and within the blood. Kinins can be divided in two major subgroups of naturally occurring peptides namely bradykinin (BK), kallidin (LysBK), [Hyp$^3$]-BK and Lys[Hyp$^3$]-BK and their respective bioactive metabolites produced by carboxypeptidases M and N (alias kininases I), desArg$^9$BK, LysdesArg$^9$BK, [Hyp$^3$]-desArg$^9$BK and Lys[Hyp$^3$]-desArg$^9$BK. Actions of bradykinin and congeners and desArg$^9$-related peptides are relayed via specific receptors referred to as $B_2$ and $B_1$, respectively, which are ubiquitously expressed on cell membranes in the affected tissues. Kinin $B_2$ and $B_1$ receptors are found in a variety of cells as endothelia, smooth muscles, epithelia, white blood cells. They mediate vascular smooth muscle relaxation via release of autacoids, particularly from the endothelium. This function provides the basic mechanism of peripheral vasodilatation which is responsible for a large part of their in vivo hypotensive effect (Duka et al., 2006, Am J Physiol Endocrinol Metab [Epub ahead of print]).

Contrary to $B_2$ receptors which are constitutively expressed, the $B_1$ receptors are usually not found in physiological conditions but is induced by various stimuli (i.e. cytokines) in several cell types including vascular endothelial and smooth muscle cells, fibroblasts, neurons. Inducible $B_1$ receptors are involved in various types of vascular inflammation associated with diabetic, hypertensive conditions, and angiogenesis. The beneficial and protecting roles of kinin $B_1$ receptors in cardiovascular-related physiopathology have been recently reviewed (Couture and Girolami, vide supra). The induction of $B_1$ receptor and subsequent activation may be seen as self-defense mechanism elicited by the vasculature against recurrent deleterious ischemic/hypoxic episodes. This view is supported by several lines of evidence. Exogenous perfusion of naturally-occurring $B_1$ receptor agonist desArg$^9$BK prior ischemic conditions, in a Langerdorff setup, decreased arrhythmias (Chahine et al., 1993, Brit J Pharmacol 108, 318-322) and protected endothelial functions in coronary arteries in the follow-up reperfusion process (Bouchard et al., 1998, Brit J Pharmacol 123, 413-420). In addition, systemic supplementation of a stable desArg$^9$BK-related analogue caused a reparative angiogenesis in a murine of limb ischemia (Emanueli et al., 2002, Circulation 105, 360-366). The involvement of newly expressed $B_1$ receptors in reparative angiogenesis of wounded arteries was equally seen in an animal model of balloon angioplasty (Pruneau et al., 1994, Brit J Pharmacol 111, 1029-1034; Agata et al., 2000, Hypertension 36, 364-370). Also, the important role of $B_1$ receptors in preservation of cardiac function after myocardial infarction has recently been demonstrated using kinin $B_1$ receptor gene knockout mice (Xu et al., 2005, Hypertension 45, 747-753)

These salutary actions, within macro- and micro-vascular networks, lies in part on capacity of kinins including desArg$^9$-BK derivatives to promote the release of nitric oxide and prostaglandins, which may serve as cytoprotective, angiogenic and dilatory factors thereby preserving functions and oxygenation of vital organs (Kichuk et al., 1996, Circulation 94, 44-51; Emanueli et al. vide supra; Sharma and Thani, 2004, IDrugs 7, 926-934). However, naturally-occurring $B_1$ receptor agonists LysdesArg$^9$BK and desArg$^9$BK as many other endogenous peptide hormones, are subjected to rapid proteolysis by tissue and plasma enzymes, which limit their therapeutic potential (Rhaleb et al., 1990, Brit J Pharmacol 99, 445-448; Drapeau et al., 1991, J Pharmacol Exp Ther 259, 997-1003). There is therefore a need for metabolically stable and potent compounds with long duration of action capable of selectively activating $B_1$ receptors which interestingly, are not prone to desensitization after exposure with their cognate ligands. Compounds of the present invention may be pharmacologically exploited for post-ischemic healing (Couture and Girolami, vide supra; Emanueli et al. vide supra; Hagiwara et al. vide supra; Duguay et al., 2004, Brit J Pharmacol 141(4), 728-736; Emanueli and Madeddu, 2001, Trends Pharmacol. Sci. 22(9), 478-484; Parenti et al., 2001, FASEB J 15(8), 1487-1489).

SUMMARY OF THE INVENTION

The present invention relates to new biologically active peptides derivatives of the general formula (1) which act as agonists at the kinin $B_1$ receptors:

$$aa^y\text{-}aa^x\text{-}aa^0\text{-}aa^1\text{-}aa^2\text{-}aa^3\text{-}aa^4\text{-}aa^5\text{-}Ser^6\text{-}Pro^7\text{-}D\text{-}Phe^8\text{-}X \quad (1)$$

wherein:

X is OH or $NH_2$ $aa^y$ is Sar, acetyl or other acyl group;

$aa^x$ is Arg, Lys, Orn (L- or D-configuration) or another basic amino acid of the L- or D-configuration, L- or D-Cit or not substituted at this position;

$aa^0$ is Arg, Lys, Orn (L or D-configuration) or another basic amino acid of the L- or D-configuration, L- or D-Cit or not substituted at this position;

$aa^1$ is Arg or D-Arg;

$aa^2$ is Pro, Oic, or another Pro-mimic amino acid, Hyp, α-(Me)Pro or another Pro-mimic amino acid derivative;

$aa^3$ is Pro, or another Pro-mimic amino acid, Hyp, Oic, α-(Me)Pro or another Pro-mimic amino acid derivative;

$aa^4$ is Gly, ethyl amine, or Aib;

$aa^5$ is Phe, Acc, Cha, Chg, Cpg, Igl, Pen, 4Bip, Phg or Thi; and

D-Phe$^8$ is D-Phe or α-(Me)Phe.

According to the above formula, residues -$aa^2$-$aa^3$-$aa^4$- may be replaced by an aliphatic ω-amino carboxyl (8 carbons chain length) linkers, and residues -$aa^2$-$aa^3$-$aa^4$-Phe$^5$- may be replaced by an aliphatic ω-amino carboxyl (11 carbons chain length) linkers.

Thus the present invention relates to peptide derivatives acting as selective agonists toward $B_1$ receptor, that at least 1) have good to high affinity and selectivity for the $B_1$ receptor, and represent long lasting B1 receptor agonists.

2) are more resistant to in vitro and in vivo enzymatic degradation.

3) have pharmacokinetic properties superior to those of naturally occurring agents.

All references referred herein are hereby incorporated by reference.

For the purpose of the present invention the following abbreviations are defined in Table 1 below.

As used herein, abbreviations of natural α-amino acids are those accepted in the art (IUPAC-IUB Commission on Biochemical Nomenclature: Symbols for amino acids derivatives and peptides 1972. Biochem J 126, 773-780), and unless prefix with D are all L-configuration.

TABLE 1

| | |
|---|---|
| Ac | Acetyl |
| acyl | $C_nH_{2n+1}$—CO—, where: n = 2-15 |
| Aib | α-aminoisobutyric acid |
| Acc | 1-amino-1-cyclopentane carboxylic acid |
| Boc | tert-butyloxy carbonyl |
| Cit | Citrulline |
| Cha | β-cyclohexyl-alanine |
| Chg | α-cyclohexyl-glycine |
| Cpg | α-cyclopentyl-glycine |
| 4Bip | 4-Phenyl-phenylalanine |
| DBU | diazabicyclo[5.4.0] undec-7-ene |
| DCC | Dicyclohexylcarbodiimide |
| DCM | dichloromethane |
| DIAD | diisopropyl azodicarbonate |
| DIEA | N,N-diisopropylethyl amine |

TABLE 1-continued

| | |
|---|---|
| DME | 1,2-dimethoxyethane |
| DMF | N,N-dimethylformamide |
| Fmoc | 9-fluorenylmethoxycarbonyl |
| HATU | O-(7-Azabenzotriazol-1-yl)-1,1,3,3-tetramethyluronium hexafluorophosphate |
| Hyp | trans-4-hydroxy-Pro |
| Igl | α-indanylglycine |
| Me | Methyl |
| α-(Me)Phe | α-methyl-phenylalanine |
| α-(Me)Pro | α-methyl-proline |
| o-NBS | ortho-nitrobenzenesulfonyl |
| NMO | N-methylmorpholine oxide |
| Pen | Penicillamine |
| Phg | Phenylglycine |
| Pro-mimic | 5,5-dimethylthiazolidine-4-carboxylic acid; 3,4-dehydro-proline; azetidine-2-carboxylic acid; trans-4-cyano-proline; cis-4-cyano-proline; 2-ethylthiazolidine-4-carboxylic acid; thiazolidine-2-carboxylic acid; 2-methylthiazolidine-4-carboxylic acid; 3-phenylpyrrolidine-2-carboxylic acid |
| Oic | (2S,3aS,7aS)-1-octahydro-1H-indole-2-carboxylic acid |
| Orn | Ornithine |
| Sar | Sarcosine |
| TBTU | O-(benzotriazol-1-yl)-1,1,3,3-tetramethyluronium tetrafluoroborate |
| Thi | β-(2-thienyl)-alanine |
| TIPS | triisopropyl silane |
| TFA | trifluoroacetic acid |
| TPP | Triphenylphosphine |

DETAILED DESCRIPTION OF THE INVENTION

Preferred $B_1$ receptor peptide agonists of the present invention may be illustrated by the following Tables 2 and 3.

TABLE 2

| | $aa^y$ | $aa^x$ | $aa^0$ | $Arg^1$ | $Aa^2$ | $aa^3$ | $aa^4$ | $aa^5$ | $Ser^6$ | $Pro^7$ | $D-Phe^8$ |
|---|---|---|---|---|---|---|---|---|---|---|---|
| 1 | | | | | | | | | | | |
| 2 | Ac | | | Arg | Pro | Pro | Gly | Phe | Ser | Pro | D-Phe |
| 3 | acyl | | | Arg | Pro | Pro | Gly | Phe | Ser | Pro | D-Phe |
| 4 | Sar | | Arg (L or D) | Arg | Pro | Pro | Gly | Phe | Ser | Pro | D-Phe |
| 5 | Ac | | Arg (L or D) | Arg | Pro | Pro | Gly | Phe | Ser | Pro | D-Phe |
| 6 | acyl | | Arg (L or D) | Arg | Pro | Pro | Gly | Phe | Ser | Pro | D-Phe |
| 7 | Sar | | Arg (L or D) | Arg | Pro | Hyp | Gly | Phe | Ser | Pro | D-Phe |
| 8 | Ac | | Arg (L or D) | Arg | Pro | Hyp | Gly | Phe | Ser | Pro | D-Phe |
| 9 | acyl | | Arg (L or D) | Arg | Pro | Hyp | Gly | Phe | Ser | Pro | D-Phe |
| 10 | Sar | | Lys (L or D) | Arg | Pro | Hyp | Gly | Phe | Ser | Pro | D-Phe |
| 11 | Ac | | Lys (L or D) | Arg | Pro | Hyp | Gly | Phe | Ser | Pro | D-Phe |
| 12 | acyl | | Lys (L or D) | Arg | Pro | Hyp | Gly | Phe | Ser | Pro | D-Phe |
| 13 | Sar | | Orn (L or D) | Arg | Pro | Pro | Gly | Phe | Ser | Pro | D-Phe |
| 14a | acyl | Arg (L or D) | Arg (L or D) | Arg | Pro | Pro | Gly | Phe | Ser | Pro | D-Phe |
| 14b | Sar | Arg (L or D) | Arg (L or D) | Arg | Pro | Pro | Gly | Phe | Ser | Pro | D-Phe |
| 15a | Ac | Lys (L or D) | Lys (L or D) | Arg | Pro | Pro | Gly | Phe | Ser | Pro | D-Phe |
| 15b | Sar | Lys (L or D) | Lys (L or D) | Arg | Pro | Pro | Gly | Phe | Ser | Pro | D-Phe |
| 16 | Sar | | Lys or Arg | Arg | Pro | Pro or Hyp | Gly | Acc | Ser | Pro | D-Phe |
| 17 | Sar | | Lys or Arg | Arg | Pro | Pro or Hyp | Gly | 4Bip | Ser | Pro | D-Phe |
| 18 | Sar | | Lys or Arg | Arg | Pro | Pro or Hyp | Gly | Cha | Ser | Pro | D-Phe |
| 19 | Sar | | Lys or Arg | Arg | Pro | Pro or Hyp | Gly | Pen | Ser | Pro | D-Phe |
| 20 | Sar | | Lys or Arg | Arg | Pro | Pro or Hyp | Gly | Thi | Ser | Pro | D-Phe |
| 21 | Sar | | Lys or Arg | Arg | Pro | Pro or Hyp | Gly | Cpg | Ser | Pro | D-Phe |
| 22 | Sar | | Lys or Arg | Arg | Pro | Pro or Hyp | Gly | Chg | Ser | Pro | D-Phe |
| 23 | Sar | | Lys or Arg | Arg | Pro | Pro or Hyp | Gly | Phg | Ser | Pro | D-Phe |
| 24 | Sar | | Lys or Arg | Arg | NH—$(CH_2)_7$—CO | | | Phe | Ser | Pro | D-Phe |
| 25 | Ac | | Lys or Arg | Arg | NH—$(CH_2)_7$—CO | | | Phe | Ser | Pro | D-Phe |
| 26a | Sar | | Orn | Arg | NH—$(CH_2)_7$—CO | | | Phe | Ser | Pro | D-Phe |
| 26b | Ac | | Orn | Arg | NH—$(CH_2)_7$—CO | | | Phe | Ser | Pro | D-Phe |
| 27 | Sar | | Lys or Arg | Arg | NH—$(CH_2)_{10}$—CO | | | | Ser | Pro | D-Phe |
| 28 | Ac | | Lys or Arg | Arg | NH—$(CH_2)_{10}$—CO | | | | Ser | Pro | D-Phe |
| 29 | Sar | | Orn | Arg | NH—$(CH_2)_{10}$—CO | | | | Ser | Pro | D-Phe |
| 30 | Ac | | Orn | Arg | NH—$(CH_2)_{10}$—CO | | | | Ser | Pro | D-Phe |

TABLE 3

| | |
|---|---|
| 2 | AcArgProProGlyPheSerProD-Phe-X |
| 3 | acylArgProProGlyPheSerProD-Phe-X |
| 4a | SarArgArgProProGlyPheSerProD-Phe-X |
| 4b | SarD-ArgArgProProGlyPheSerProD-Phe-X |
| 5a | AcArgArgProProGlyPheSerProD-Phe-X |
| 5b | AcD-ArgArgProProGlyPheSerProD-Phe-X |
| 6a | acylArgArgProProGlyPheSerProD-Phe-X |
| 6b | acylD-ArgArgProProGlyPheSerProD-Phe-X |
| 7a | SarArgArgProHypGlyPheSerProD-Phe-X |
| 7b | SarD-ArgArgProHypGlyPheSerProD-Phe-X |
| 8a | AcArgArgProHypGlyPheSerProD-Phe-X |
| 8b | AcD-ArgArgProHypGlyPheSerProD-Phe-X |
| 9a | acylArgArgProHypGlyPheSerProD-Phe-X |
| 9b | acylD-ArgArgProHypGlyPheSerProD-Phe-X |
| 10a | SarLysArgProHypGlyPheSerProD-Phe-X |
| 10b | SarD-LysArgProHypGlyPheSerProD-Phe-X |
| 11a | AcLysArgProHypGlyPheSerProD-Phe-X |
| 11b | AcD-LysArgProHypGlyPheSerProD-Phe-X |
| 12a | acylLysArgProHypGlyPheSerProD-Phe-X |
| 12b | acylD-LysArgProHypGlyPheSerProD-Phe-X |
| 13a | SarOrnArgProProGlyPheSerProD-Phe-X |
| 13b | SarD-OrnArgProProGlyPheSerProD-Phe-X |
| 14a | acylArgArgArgProProGlyPheSerProD-Phe-X |
| 14b | acylD-ArgArgArgProProGlyPheSerProD-Phe-X |
| 14c | acylArgD-ArgArgProProGlyPheSerProD-Phe-X |
| 14d | acylD-ArgD-ArgArgProProGlyPheSerProD-Phe-X |
| 14ba | SarArgArgArgProProGlyPheSerProD-Phe-X |
| 14bb | SarD-ArgArgArgProProGlyPheSerProD-Phe-X |
| 14bc | SarArgD-ArgArgProProGlyPheSerProD-Phe-X |
| 14bd | SarD-ArgD-ArgArgProProGlyPheSerProD-Phe-X |
| 15a | AcLysLysArgProProGlyPheSerProD-Phe-X |
| 15b | AcD-LysLysArgProProGlyPheSerProD-Phe-X |
| 15c | AcLysD-LysArgProProGlyPheSerProD-Phe-X |
| 15d | AcD-LysD-LysArgProProGlyPheSerProD-Phe-X |
| 15ba | SarLysLysArgProProGlyPheSerProD-Phe-X |
| 15bb | SarD-LysLysArgProProGlyPheSerProD-Phe-X |
| 15bc | SarLysD-LysArgProProGlyPheSerProD-Phe-X |
| 15bd | SarD-LysD-LysArgProProGlyPheSerProD-Phe-X |
| 16a | SarLysArgProHypGlyAccSerProD-Phe-X |
| 16b | SarArgArgProHypGlyAccSerProD-Phe-X |
| 17a | SarLysArgProHypGly4BipSerProD-Phe-X |
| 17b | SarArgArgProHypGly4BipSerProD-Phe-X |
| 18a | SarLysArgProHypGlyChaSerProD-Phe-X |
| 18b | SarArgArgProHypGlyChaSerProD-Phe-X |
| 19a | SarLysArgProHypGlyPenSerProD-Phe-X |
| 19b | SarArgArgProHypGlyPenSerProD-Phe-X |
| 20a | SarLysArgProHypGlyThiSerProD-Phe-X |
| 20b | SarArgArgProHypGlyThiSerProD-Phe-X |
| 21a | SarLysArgProHypGlyCpgSerProD-Phe-X |
| 21b | SarArgArgProHypGlyCpgSerProD-Phe-X |
| 22a | SarLysArgProHypGlyChgSerProD-Phe-X |
| 22b | SarArgArgProHypGlyChgSerProD-Phe-X |
| 23a | SarLysArgProHypGlyPhgSerProD-Phe-X |
| 23b | SarArgArgProHypGlyPhgSerProD-Phe-X |
| 24a | SarLysArgNH—(CH$_2$)$_7$—COPheSerProD-Phe-X |
| 24b | SarArgArgNH—(CH$_2$)$_7$—COPheSerProD-Phe-X |
| 25a | AcLysArgNH—(CH$_2$)$_7$—COPheSerProD-Phe-X |
| 25b | AcArgArgNH—(CH$_2$)$_7$—COPheSerProD-Phe-X |
| 26a | SarOrnArgNH—(CH$_2$)$_7$—COPheSerProD-Phe-X |
| 26b | AcOrnArgNH—(CH$_2$)$_7$—COPheSerProD-Phe-X |
| 27a | SarLysArgNH—(CH$_2$)$_{10}$—COSerProD-Phe-X |
| 27b | SarArgArgNH—(CH$_2$)$_{10}$—COSerProD-Phe-X |
| 28a | AcLysArgNH—(CH$_2$)$_{10}$—COSerProD-Phe-X |
| 28b | AcArgArgNH—(CH$_2$)$_{10}$—COSerProD-Phe-X |
| 29 | SarOrnArgNH—(CH$_2$)$_{10}$—COSerProD-Phe-X |
| 30 | AcOrnArgNH—(CH$_2$)$_{10}$—COSerProD-Phe-X |

The synthesis of peptides described herein, including the preparation of appropriate amino acid derivatives, their activation and coupling to form peptides and methods for purification of peptides and determination of their purity are included in the general body of knowledge of peptide chemistry, as generally described in "Solid phase peptide synthesis" by Stewart and Young (1984, Solid phase peptide synthesis. Pierce Chemical Company, $2^{nd}$ Edition) for the solution-phase synthesis and solid phase method.

Therapeutic applications of desArg$^9$BK-related B$_1$ receptor agonists are based upon recognized beneficial actions mediated by kinin B$_1$ receptors such as vasodilatation/hypotension, neo-vascularization, angiogenesis, anti-ischemia, increase of vascular permeability specifically in surrounding brain tumors, and include treatment of pathological conditions where amount of exogenous B$_1$ receptor agonists is needed. These conditions may include treatment of life-threatening diseases specifically hypertension and diabetes associated with vasculopathies. Compounds of the present invention may be used to prevent and/or reverse end-organ failure, owing to lack of tissue perfusion, in hypertensive and diabetic patients. Such considerations may be extended to other diseases including cerebral and coronary artery diseases, to reduce incidence of stroke and myocardial infarction, respectively, and peripheral arterial disease to improve mobility of afflicted individuals. Another therapeutic application of the present invention covers atherosclerotic coronary artery diseases where balloon angioplasty is to be performed to restore blood flow to blood-deprived heart tissue. Restenosis (repeat narrowing or blockage) of injured heart coronary vessels is frequently observed, usually one-third of the time, following angioplasty procedure. Kinin B$_1$ receptors stimulants, owing to their angiogenic properties, may assist to lower the rate of recurrence or restenosis.

Limited therapeutic success in the treatment of central nervous system neoplasia with chemotherapy is attributed partly by delivery impediment related to blood brain barrier. Different approaches have been advocated to improve delivery across the blood brain barrier (Black, 1995, Adv Drug Delivery Rev 15, 37-52). Amongst these approaches, the infusion of proteolytically resistant bradykinin and desArg$^9$BK surrogates to modulate permeability of the neoplastic blood vessels, have been studied (Emerich et al., 2000, Pharm Res 17, 1212-1219; Cardoso et al., 2004, BMC Neurosci 5, 38). Pharmacological approach, using kinin B$_2$ receptor synthetic peptide agonist, has also prove successful for delivery of chemotherapeutics to solid peripheral tumors thereby increasing their efficacy (Emerich et al., 2001, J Pharmacol Exp Ther 296, 623-631). Altogether, these findings underscore the kinin B$_1$ (and B$_2$) receptors as potential targets to cure and/or to improve the quality of life of cancer patients.

Compounds of the present invention may be administered topically, subcutaneously, or by injection or infusion or delivered using suited biodegradable microsphere-based carrier systems or as an oral suspension in an appropriate vehicle or as tablets, pills, capsules, caplets or the like. The dosage regimen and manner of administration will be defined by the application of the B$_1$ receptor peptide agonists and as per standard clinical testing to find the optimal dose.

The present invention will be more readily understood by referring to the following examples which are given to illustrate the invention rather than to limit its scope.

Example 1

Peptide Synthesis

Synthesis of the kinin B$_1$ receptor agonists of the present invention by solid phase peptide synthesis (SPPS) may be carried out manually (see Stewart & Young and K. Wisniewski) or by use of the Applied Bioscience 430A for Boc-amino acids or by use of Pioneer™ continuous flow peptide synthesis system for Fmoc-amino acids. SPPS involves use of standard procedures, defined as follows:
General Method Involving Boc-Strategy
Procedure A, DCC coupling reaction: A 4-fold excess of Boc-amino acids over resin substitution rate is used in the Applied Bioscience 430A synthesizer. Boc-amino acids are activated for coupling with an equimolar amount of DCC and 2 equivalents of DIEA. The solvent may be DCM, DMF, or NMP. The resin is washed with the same solvent before and after coupling. Completeness of coupling is determined with a Kaiser test.

Procedure B, TFA deprotection and neutralization: The deprotection reagent is 40% TFA in DCM, containing 1 mg/mL N-acetyl-LD-tryptophan. It is used for 30 min, following a prewash. The neutralization reagent is 20% DIEA in DCM.

Procedure C, N-Terminal acylation: A 5-fold excess of acyl chlorides and 10-fold excess of DIEA over peptide-resin are used in DCM for 30 min. The resin is washed with the same solvent after completion of the reaction.

Procedure D, HF cleavage: A batch of 0.5 mmole of peptide-resin is mixed with 1.0 mL anisole and chilled in the reaction vessel (resistant to HF) to −78° C., and 10 ml of anhydrous HF is distilled into the vessel under vacuum. The mixture is stirred at 0° C. for 1 h, and the HF is evaporated first under a nitrogen flow, then under vacuum. The peptide and resin mixture is washed three times with dry ether, and the peptide is extracted into 50% acetic acid. The peptide solution is concentrated under vacuum, diluted in water, and lyophilized.

Procedure E, Purification: Preparative medium pressure chromatography may be carried out on a reversed phase C18 silica column in a gradient of 0.1% TFA in water to 0.05% TFA in acetonitrile. Eluted peptide is detected by UV at 254 nm. Analytical HPLC may be carried out in the same system to identified pure fractions.

Procedure F, Characterization: Final products are identified by analytical HPLC and by mass spectroscopy. MALDI spectra are recorded on a Tofspec™ 2E (micromass, UK).

General Method Involving Fmoc-Strategy

The approach is an alternative approach of peptides synthesis and standard with Mitsunobu reaction ω-amino acids residues. Synthesis may be carried out by use of Pioneer™ continuous flow peptide synthesis system.

Procedure G: The resin is placed in the column and a 2 to 4-fold excess of Fmoc-protected amino acids over resin substitution rate is placed in the sampler tray. Synthesis is performed using amine free DMF. All solutions needed for the solid phase continuous flow synthesis are prepared and loaded in the synthesizer. The synthesis protocol is prepared, loaded into the synthesizer, and run in normal or extended cycle mode. Fmoc deprotection is performed in 20% piperidine in DMF and monitored through UV detector at 364 nm. Fmoc-protected amino acids are activated for coupling with an equimolar amount of HATU or TBTU, and 2 equivalents of DIEA.

Procedure H, N-terminal caping (acetylation): This step is optional and can be included in the synthesis protocol. The acetylation reagents are 5% acetic anhydride and 6% 2,4-lutidine in DMF. The resin is washed with the same solvent and isopropanol after completion of the reaction. The resin is removed from the column synthesizer and dried under vacuum 12 hours.

Procedure I, TFA cleavage: The cleavage solution, TFA:water:TIPS (95%:2.5%:2.5%), is mixed with peptide-resin, and stirred at room temperature for 2 h. The resin is filtrated and the peptide is precipitated in dry ether. The suspension is centrifuged. The ether solution is decanted and the precipitated peptide is dissolved in water and lyophilized. The peptide is purified and characterized as described in procedures E and F.

Example 2

Synthesis of N-Terminal Alkylated Analogues

The peptide chain is assembled by Fmoc strategy. O-NBS group is introduced after Fmoc deprotection at the N-terminal position as described in procedure J followed by 0.1 mmol of o-NBS-aa$_n$-resin (0.2-0.6 mmol/g) is suspended in 1 mL of DME, and 1 mmol of appropriate alcohol is added to the suspension. Mitsunobu reaction and deprotection of the o-NBS group are performed as described in procedure J. After the desired peptide is assembled, the resin is treated with 10 equivalent of 1 M solution of mercaptoethanol/DBU in DMF for 1 h, and washed thoroughly with DMF and DCM. The peptide is then cleaved with an appropriate TFA cocktail, see procedure 1. The peptide is purified and characterized as described in procedures E and F.

Example 3

Functional Assays

In vitro and in vivo bioassays were used to assess the potency and selectivity indexes of peptide compounds at the inducible kinin $B_1$ receptor subtype.

In Vitro Functional Assays (Isolated Preparations in Organ Baths)

Selected compounds were tested for activities in three isolated vessels: the rabbit aorta (rbA) and jugular vein (rbJV) and the human umbilical vein (hUV). All details regarding the collection and handling of human umbilical cords and rabbit vessels as well as, the procedures for preparing the isolated organs and the experimental protocols are described in these publications: (Gobeil et al., 1996, Br J Pharmacol 118, 289-294; Gobeil et al., 1999, Hypertension 33(3), 823-829). The rbA and the hUV without endothelium (which contains $B_1$ receptors) were used to determine the agonistic activities of each compound expressed in term of pEC$_{50}$ values (−log of the molar concentration of agonist required to produce 50% of the maximal response). The rabbit jugular vein (which contains only $B_2$ receptor) was used to exclude any action of the new compounds at $B_2$ receptors and thus establish their selectivity.

In vivo Functional Assays (Rabbit Blood Pressure Model)

Selected compounds were tested as hypotensive agents in anesthetized rabbits. Surgical procedures and experimental methodologies used herein are based upon previous detailed reports (Gobeil et al., 1999, Immunopharmacol 43: 179-185; Gobeil et al., vide supra). Pathogen-free rabbits (which do not express functional $B_1$ receptors) were anesthetized with a mixed solution of ketamine/xylazine injected intramuscularly in experiments designed to study possible interaction of the compounds with $B_2$ receptors. The trachea was intubated to facilitate breathing. Mean arterial blood pressure was continuously monitored by inserting a polyethylene catheter (filled with heparinized saline solution) into the right carotid artery attached to a transducer (model TDX-300; Micro-Med. Inc., KY, USA) connected to a blood pressure analyzer (model BPA-400a; Micro-Med Inc., KY, USA). A second arterectomy was performed on the left carotid artery for the administration of graded doses of compounds into the aorta. In experiments designed to study potency of compounds at $B_1$ receptors in rabbits, the anesthetic sodium pentobarbital (30 mg/kg intravenously (i.v.) through the auricular vein) was used instead of the ketamine/xylasine solution. For this purpose, rabbits were immunostimulated with lipopolysaccharide (LPS) (50 μg/kg i.v.) 5 hr before inducing the anesthesia;

this endotoxin is a well known potent inducer of $B_1$ receptor expression both in vitro and in vivo experiments. Hypotensive activities and duration of action of peptide compounds were measured following their intra-aortic administration as described in Gobeil et al. (1999, Hypertension 33(3), 823-829).

Example 4

Enzymatic Stability Studies

Enzymatic resistance of peptide compounds were measured in harsh conditions using rabbit lung and kidney extracts prepared as reported (Tramontana et al., 2001, J Pharmacol Exp Ther 296(3), 1051-1057) with minor modifications. Briefly, animals were euthanized, organs harvested and cleaned from connective and adipose tissues. Tissues were then homogenized with a Polytron homogenizer in 5 volumes (w/v) of cold buffer consisting of Tris HCl 50 mM pH 7.5, NaCl 300 mM and $ZnCl_2$ 10 μM, and centrifuged at 1500 g for 15 min at 4° C. Concentration of proteins from the resulting supernatant was determined using Bradford method with bovine serum as standard. Peptide compounds (150 μM) were incubated at 37° C. in the presence of tissue enzymatic extracts (200 μg proteins) for different times (0, 15, 60 min) in a total reaction medium of 250 μl. The naturally-occurring $B_1$ receptor agonist LysdesArg$^9$-BK served as reference peptide. Hydrolysis was stopped by immersing samples in boiling water.

Separation of peptide substrates and their metabolites was achieved by reverse-phase HPLC on a $C_{18}$ μBondpak column (Waters Associates) with a linear gradient of 5% to 65% of water/acetonitrile (both containing 0.05% TFA) at 1 mL/min over a period of 20 min, as described (Gobeil et al., 1999, vide supra). A 50 μL aliquot of each assay was injected into the column. Peptide metabolism was calculated from the decrease in peptide substrate concentration. The elution positions of the peptides were determined following the absorbance at 214 nm and peak area integration was calculated using a computer software program (Baseline 810, Waters).

Example 5

Blood Brain Barrier Opening

The delivery potency of peptide compounds was studied in syngeneic F98-Fischer glioma rat model based on previous reports (Barth, 1998, J Neurooncol 36, 91-102; Mathieu et al., 2005, The J Appl Res 5(1), 17-25). Briefly, the F98 cell line was cultured in monolayer and stereotactically implanted ($1 \times 10^4$ cells in a volume of 5 μl; 1 μl/min) in the right frontal lobe of Fischer rats using standardized and validated coordinates. In this model, the tumor take has been shown to be 100%. Moreover, this model has been shown to adequately emulate the situation of primary malignant brain tumors in the human (Mathieu et al., vide supra). At 14 days post-implantation, rats were anesthetized with ketamine/xylazine solution. Blood brain barrier disruption was performed in rats by administering specific $B_1$ interacting peptides or vehicle (isotonic saline) into the internal carotid artery in a retrograde fashion from the external carotid after catheter implantation. The infusion rates of peptide or vehicle (total volume injected: 500 μl) were set at 10 nmol/kg/min for 5 min followed by a 20 min resting period. Animals were perfused via the same catheter using paraformaldehyde/glutaraldehyde solution. Brain tissues were then collected, embedded in paraffin, sectioned (3 μm) using a dedicated brain matrix and prepared for immunohistochemistry for albumin quantification (as marker of the extent of barrier opening) (Fortin, 2003, Prokai L, Prokai-Tatrai K eds. Peptide transport and delivery to the CNS. Progress in drug research, Birkhauser, Switzerland, 61, 127-154). This quantification was expressed as the ratio of immunostaining regions against the treated cerebral hemisphere (Fortin, 2003, vide supra).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

REFERENCES

IUPAC-IUB Commission on Biochemical Nomenclature: Symbols for amino acids derivatives and peptides 1972. Biochem J 126, 773-780
Agata et al., 2000, Hypertension 36, 364-370
Barth, 1998, J Neurooncol 36, 91-102
Black, 1995, Adv Drug Delivery Rev 15, 37-52
Bouchard et al., 1998, Brit J Pharmacol 123, 413-420
Cardoso et al., 2004, BMC Neurosci 5, 38
Chahine et al., 1993, Brit J Pharmacol 108, 318-322
Couture and Girolami, 2004, Eur J Pharmacol 500 (1-3), 467-485
Drapeau et al., 1991, J Pharmacol Exp Ther 259, 997-1003
Duguay et al., 2004, Brit J Pharmacol 141(4), 728-736
Duka et al., 2001, Circ Res 88, 275-281
Duka et al., 2006, Am J Physiol Endocrinol Metab [Epub ahead of print]
Emanueli and Madeddu, 2001, Trends Pharmacol. Sci. 22(9), 478-484
Emanueli et al., 2002, Circulation 105, 360-366
Emerich et al., 2000, Pharm Res 17, 1212-1219
Emerich et al., 2001, J Pharmacol Exp Ther 296, 623-631
Fortin, 2003, Prokai L, Prokai-Tatrai K eds. Peptide transport and delivery to the CNS, Progress in drug research, Birkhauser, Switzerland, 61, 127-154
Gobeil et al., 1996, Br J Pharmacol 118, 289-294
Gobeil et al., 1999, Immunopharmacol 43, 179-185
Gobeil et al., 1999, Hypertension 33(3), 823-829
Hagiwara et al., 2004, Hypertens Res 27(6), 399-408
Kichuk et al., 1996, Circulation 94, 44-51
Mathieu et al., 2005, The J Appl Res 5(1), 17-25
Parenti et al., 2001, FASEB J 15(8), 1487-1489
Pruneau et al., 1994, Brit J Pharmacol 111, 1029-1034
Rhaleb et al., 1990, Brit J Pharmacol 99, 445-448
Sharma and Thani, 2004, Drug 7(10): 926-934
Stewart and Young, 1984, Solid phase peptide synthesis. Pierce Chemical Company, $2^{nd}$ Edition
Tramontana et al., 2001, J Pharmacol Exp Ther 296(3), 1051-1057
Xu et al., 2005, Hypertension 45(4): 747-753

The invention claimed is:
1. A compound of formula (1)

$$aa^y\text{-}aa^x\text{-}aa^0\text{-}aa^1\text{-}aa^2\text{-}aa^3\text{-}aa^4\text{-}aa^5\text{-}Ser^6\text{-}Pro^7\text{-}D\text{-}Phe^8\text{-}X \quad (1)$$

or a salt thereof;
  wherein:
  X is OH or $NH_2$;
  $aa^y$ is Sar, acetyl or other acyl group;

aa^x is L-Arg, D-Arg, L-Lys, D-Lys, L-Orn, D-Orn, another basic amino acid of the L or D-configuration, L-Cit, D-Cit or is absent;

aa^0 is L-Arg, D-Arg, L-Lys, D-Lys, L-Orn, D-Orn, another basic amino acid of the L or D-configuration, or L-Cit, D-Cit;

aa^1 is L-Arg or D-Arg;

aa^2 is L-Pro, L-Oic, another L-Pro mimic amino acid, L-Hyp, L-α-(Me)Pro or another Pro-mimic amino acid derivative chosen from 5,5-dimethylthiazolidine-4-carboxylic acid; 3,4-dehydro-proline; azetidine-2-carboxylic acid; trans-4-cyano-proline; cis-4-cyano-proline; 2-ethylthiazolidine-4-carboxylic acid; thiazolidine-2-carboxylic acid; 2-methylthiazolidine-4-carboxylic acid; and 3-phenylpyrrolidine-2-carboxylic acid;

aa^3 is L-Pro, or another L-Pro-mimic amino acid, L-Hyp, L-Oic, L-α-(Me)Pro or another Pro-mimic amino acid derivative chosen from 5,5-dimethylthiazolidine-4-carboxylic acid; 3,4-dehydro-proline; azetidine-2-carboxylic acid; trans-4-cyano-proline; cis-4-cyano-proline; 2-ethylthiazolidine-4-carboxylic acid; thiazolidine-2-carboxylic acid; 2-methylthiazolidine-4-carboxylic acid; and 3-phenylpyrrolidine-2-carboxylic acid;

aa^4 is Gly, ethyl amine, or Aib;

aa^5 is L-Phe, D-Phe, Acc, L-Cha, D-Cha, L-Chg, D-Chg, L-Cpg, D-Cpg, L-Igl, D-Igl, L-Pen, D-Pen, L-4Bip, D-4Bip, L-Phg, D-Phg, L-Thi, or D-Thi; and D-Phe^8 is D-Phe;

or

-aa^2-aa^3-aa^4- is an aliphatic ω-amino carboxyl residue with a chain length of 8 carbon atoms; and X, aa^y, aa^x, aa^0, aa^1, aa^5, and D-Phe^8 are as previously defined;

or

-aa^2-aa^3-aa^4-aa^5- is an aliphatic ω-amino carboxyl residue with a chain length of 11 carbon atoms; and X, aa^y, aa^x, aa^0, aa^1, and D-Phe^8 are as previously defined.

2. The compound of claim 1, wherein said compound is in a free base form.

3. The compound of claim 1, wherein:

X is OH or NH_2;

aa^y is Sar, acetyl or other acyl group;

aa^x is L-Arg, D-Arg, L-Lys, D-Lys, L-Orn, D-Orn, another basic amino acid of the L or D-configuration, L-Cit, D-Cit or is absent;

aa^0 is L-Arg, D-Arg, L-Lys, D-Lys, L-Orn, D-Orn, another basic amino acid of the L or D-configuration, or L-Cit, D-Cit;

aa^1 is L-Arg or D-Arg;

aa^2 is L-Pro, L-Oic, another L-Pro mimic amino acid, L-Hyp, L-α-(Me)Pro or another Pro-mimic amino acid derivative chosen from 5,5-dimethylthiazolidine-4-carboxylic acid; 3,4-dehydro-proline; azetidine-2-carboxylic acid; trans-4-cyano-proline; cis-4-cyano-proline; 2-ethylthiazolidine-4-carboxylic acid; thiazolidine-2-carboxylic acid; 2-methylthiazolidine-4-carboxylic acid; and 3-phenylpyrrolidine-2-carboxylic acid;

aa^3 is L-Pro, or another L-Pro-mimic amino acid, L-Hyp, L-Oic, L-α-(Me)Pro or another Pro-mimic amino acid derivative chosen from 5,5-dimethylthiazolidine-4-carboxylic acid; 3,4-dehydro-proline; azetidine-2-carboxylic acid; trans-4-cyano-proline; cis-4-cyano-proline; 2-ethylthiazolidine-4-carboxylic acid; thiazolidine-2-carboxylic acid; 2-methylthiazolidine-4-carboxylic acid; and 3-phenylpyrrolidine-2-carboxylic acid;

aa^4 is Gly, ethyl amine, or Aib;

aa^5 is L-Phe, Acc, L-Cha, L-Chg, L-Cpg, L-Igl, L-Pen, L-4Bip, L-Phg, or L-Thi; and D-Phe^8 is D-Phe.

4. The compound of claim 3, wherein said compound is chosen from:

SarArgArgProProGlyPheSerProD-Phe-X
SarD-ArgArgProProGlyPheSerProD-Phe-X
AcArgArgProProGlyPheSerProD-Phe-X
AcD-ArgArgProProGlyPheSerProD-Phe-X
acylArgArgProProGlyPheSerProD-Phe-X
acylD-ArgArgProProGlyPheSerProD-Phe-X
SarArgArgProHypGlyPheSerProD-Phe-X
SarD-ArgArgProHypGlyPheSerProD-Phe-X
AcArgArgProHypGlyPheSerProD-Phe-X
AcD-ArgArgProHypGlyPheSerProD-Phe-X
acylArgArgProHypGlyPheSerProD-Phe-X
acylD-ArgArgProHypGlyPheSerProD-Phe-X
SarLysArgProHypGlyPheSerProD-Phe-X
SarD-LysArgProHypGlyPheSerProD-Phe-X
AcLysArgProHypGlyPheSerProD-Phe-X
AcD-LysArgProHypGlyPheSerProD-Phe-X
acylLysArgProHypGlyPheSerProD-Phe-X
acylD-LysArgProHypGlyPheSerProD-Phe-X
SarOrnArgProProGlyPheSerProD-Phe-X
SarD-OrnArgProProGlyPheSerProD-Phe-X
acylArgArgProProGlyPheSerProD-Phe-X
acylD-ArgArgArgProProGlyPheSerProD-Phe-X
acylArgD-ArgArgProProGlyPheSerProD-Phe-X
acylD-ArgD-ArgArgProProGlyPheSerProD-Phe-X
SarArgArgArgProProGlyPheSerProD-Phe-X
SarD-ArgArgArgProProGlyPheSerProD-Phe-X
SarArgD-ArgArgProProGlyPheSerProD-Phe-X
SarD-ArgD-ArgArgProProGlyPheSerProD-Phe-X
AcLysLysArgProProGlyPheSerProD-Phe-X
AcD-LysLysArgProProGlyPheSerProD-Phe-X
AcLysD-LysArgProProGlyPheSerProD-Phe-X
AcD-LysD-LysArgProProGlyPheSerProD-Phe-X
SarLysLysArgProProGlyPheSerProD-Phe-X
SarD-LysLysArgProProGlyPheSerProD-Phe-X
SarLysD-LysArgProProGlyPheSerProD-Phe-X
SarD-LysD-LysArgProProGlyPheSerProD-Phe-X
SarLysArgProHypGlyAccSerProD-Phe-X
SarArgArgProHypGlyAccSerProD-Phe-X
SarLysArgProHypGly4BipSerProD-Phe-X
SarArgArgProHypGly4BipSerProD-Phe-X
SarLysArgProHypGlyChaSerProD-Phe-X
SarArgArgProHypGlyChaSerProD-Phe-X
SarLysArgProHypGlyPenSerProD-Phe-X
SarArgArgProHypGlyPenSerProD-Phe-X
SarLysArgProHypGlyThiSerProD-Phe-X
SarArgArgProHypGlyThiSerProD-Phe-X
SarLysArgProHypGlyCpgSerProD-Phe-X
SarArgArgProHypGlyCpgSerProD-Phe-X
SarLysArgProHypGlyChgSerProD-Phe-X
SarArgArgProHypGlyChgSerProD-Phe-X
SarLysArgProHypGlyPhgSerProD-Phe-X
SarArgArgProHypGlyPhgSerProD-Phe-X
SarLysArgNH—(CH_2)_7—COPheSerProD-Phe-X
SarArgArgNH—(CH_2)_7—COPheSerProD-Phe-X
AcLysArgNH—(CH_2)_7—COPheSerProD-Phe-X
AcArgArgNH—(CH_2)_7—COPheSerProD-Phe-X
SarOrnArgNH—(CH_2)_7—COPheSerProD-Phe-X
AcOrnArgNH—(CH_2)_7—COPheSerProD-Phe-X
SarLysArgNH—(CH_2)_{10}—COSerProD-Phe-X
SarArgArgNH—(CH_2)_{10}—COSerProD-Phe-X
AcLysArgNH—(CH_2)_{10}—COSerProD-Phe-X
AcArgArgNH—(CH_2)_{10}—COSerProD-Phe-X
SarOrnArgNH—(CH_2)_{10}—COSerProD-Phe-X
AcOrnArgNH—(CH_2)_{10}—COSerProD-Phe-X
SarLysArgProHypGlyIglSerProD-Phe-X
SarArgArgProHypGlyIglSerProD-Phe-X
SarLysArgProHypGlyCpgSerProD-Phe-X

```
SarArgArgProHypGlyIcpgSerProD-Phe-X
SarLysArgProHypGlyID-CpgSerProD-Phe-X and
SarArgArgProHypGlyID-CpgSerProD-Phe-X.
```

5. A pharmaceutical composition for therapy of hypertension, comprising a therapeutically effective amount of a compound of claim 1 and a pharmaceutically acceptable carrier.

6. A pharmaceutical composition for enhancing delivery of a chemotherapeutic agent across the blood brain barrier, said composition comprising a therapeutically effective amount of a compound of claim 1, said chemotherapeutic agent and a pharmaceutically acceptable carrier.

7. A method for treating hypertension, said method comprising the step of administering to a patient in need thereof a compound of claim 1.

8. A method for enhancing delivery of a chemotherapeutic agent across the blood brain barrier, said method comprising administering to a patient in need thereof a compound of claim 1 and said chemotherapeutic agent.

9. The compound of claim 1, wherein:
X is OH or $NH_2$;
$aa^y$ is Sar, acetyl or other acyl group;
$aa^x$ is L-Arg, D-Arg, L-Lys, D-Lys, L-Orn, D-Orn, another basic amino acid of the L or D-configuration, L-Cit, D-Cit or is absent;
$aa^0$ is L-Arg, D-Arg, L-Lys, D-Lys, L-Orn, D-Orn, another basic amino acid of the L or D-configuration, or L-Cit, D-Cit;
$aa^1$ is L-Arg or D-Arg;
$aa^2$ is L-Pro, L-Oic, another L-Pro mimic amino acid, L-Hyp, L-α-(Me)Pro or another Pro-mimic amino acid derivative chosen from 5,5-dimethylthiazolidine-4-carboxylic acid; 3,4-dehydro-proline; azetidine-2-carboxylic acid; trans-4-cyano-proline; cis-4-cyano-proline; 2-ethylthiazolidine-4-carboxylic acid; thiazolidine-2-carboxylic acid; 2-methylthiazolidine-4-carboxylic acid; and 3-phenylpyrrolidine-2-carboxylic acid;
$aa^3$ is L-Pro, or another L-Pro-mimic amino acid, L-Hyp, L-Oic, L-α-(Me)Pro or another Pro-mimic amino acid derivative chosen from 5,5-dimethylthiazolidine-4-carboxylic acid; 3,4-dehydro-proline; azetidine-2-carboxylic acid; trans-4-cyano-proline; cis-4-cyano-proline; 2-ethylthiazolidine-4-carboxylic acid; thiazolidine-2-carboxylic acid; 2-methylthiazolidine-4-carboxylic acid; and 3-phenylpyrrolidine-2-carboxylic acid;
$aa^4$ is Gly, ethyl amine, or Aib;
$aa^5$ is L-Phe, D-Phe, Acc, L-Cha, D-Cha, L-Chg, D-Chg, L-Cpg, D-Cpg, L-Igl, D-Igl, L-Pen, D-Pen, L-4Bip, D-4Bip, L-Phg, D-Phg, L-Thi, or D-Thi; and
D-$Phe^8$ is D-Phe.

10. A compound of formula (1)

$$aa^y\text{-}aa^x\text{-}aa^0\text{-}aa^1\text{-}aa^2\text{-}aa^3\text{-}aa^4\text{-}aa^5\text{-}Ser^6\text{-}Pro^7\text{-}D\text{-}Phe^8\text{-}X \quad (1)$$

wherein:
X is OH or $NH_2$;
$aa^y$ is Sar;
$aa^x$ is L-Arg, D-Arg, L-Lys, D-Lys, L-Orn, D-Orn, L-Cit, D-Cit or is absent;
$aa^0$ is L-Arg, D-Arg, L-Lys, D-Lys, L-Orn, D-Orn, L-Cit, D-Cit or is absent;
$aa^1$ is L-Arg or D-Arg;
$aa^2$ is L-Pro, L-Oic, another L-Pro mimic amino acid, L-Hyp, L-α-(Me)Pro or another Pro-mimic amino acid derivative chosen from 5,5-dimethylthiazolidine-4-carboxylic acid; 3,4-dehydro-proline; azetidine-2-carboxylic acid; trans-4-cyano-proline; cis-4-cyano-proline; 2-ethylthiazolidine-4-carboxylic acid; thiazolidine-2-carboxylic acid; 2-methylthiazolidine-4-carboxylic acid; and 3-phenylpyrrolidine-2-carboxylic acid;
$aa^3$ is L-Pro, or another L-Pro-mimic amino acid, L-Hyp, L-Oic, L-α-(Me)Pro or another Pro-mimic amino acid derivative chosen from 5,5-dimethylthiazolidine-4-carboxylic acid; 3,4-dehydro-proline; azetidine-2-carboxylic acid; trans-4-cyano-proline; cis-4-cyano-proline; 2-ethylthiazolidine-4-carboxylic acid; thiazolidine-2-carboxylic acid; 2-methylthiazolidine-4-carboxylic acid; and 3-phenylpyrrolidine-2-carboxylic acid;
$aa^4$ is Gly, ethyl amine, or Aib;
$aa^5$ is L-Phe, D-Phe, Acc, D-Acc, L-Cha, D-Cha, L-Chg, D-Chg, L-Cpg, D-Cpg, L-Igl, D-Igl, L-Pen, D-Pen, L-4Bip, D-4Bip, L-Phg, D-Phg, L-Thi, or D-Thi; and
D-$Phe^8$ is D-Phe;
or
-$aa^2$-$aa^3$-$aa^4$- is —NH—$(CH_2)_{10}$—CO—; and X, $aa^y$, $aa^x$, $aa^0$, $aa^1$, $aa^5$, and D-$Phe^8$ are as previously defined;
or
-$aa^2$-$aa^3$-$aa^4$-$aa^5$- is —NH—$(CH_2)_{10}$—CO—; and X, $aa^y$, $aa^x$, $aa^0$, $aa^1$, and D-$Phe^8$ are as previously defined,
with the proviso that the compound of formula (1) is different than Sar[$DPhe^8$]des$Arg^9$BK.

11. The compound of claim 3, wherein said compound is chosen from:

```
SarLysArgProHypGlyChaSerProD-Phe-X
SarLysArgProHypGlyPhgSerProD-Phe-X
SarLysArgProHypGlyIglSerProD-Phe-X
SarLysArgProHypGlyPenSerProD-Phe-X       and
SarLysArgProHypGlyCpgSerProD-Phe-X.
```

12. The salt of the compound according to claim 1, wherein said salt is an acid addition salt.

13. The salt of the compound according to claim 12, wherein said acid addition salt is formed from an organic acid.

14. The salt of the compound according to claim 12, wherein said acid addition salt is formed from an inorganic acid.

15. The salt of the compound according to claim 1, wherein said salt is a base addition salt.

16. A method for delivering a chemotherapeutic agent to peripheral and brain tumors, said method comprising administering to a patient in need thereof a compound of claim 1 and said chemotherapeutic agent.

17. A method for delivering a chemotherapeutic agent to peripheral and brain tumors, said method comprising administering to a patient in need thereof a composition comprising a compound of claim 1 and said chemotherapeutic agent.

18. A method for enhancing delivery of a chemotherapeutic agent across the blood brain barrier, said method comprising administering to a patient in need thereof a composition comprising a compound of claim 1 and said chemotherapeutic agent.

* * * * *

UNITED STATES PATENT AND TRADEMARK OFFICE
CERTIFICATE OF CORRECTION

PATENT NO. : 8,076,453 B2
APPLICATION NO. : 11/916136
DATED : December 13, 2011
INVENTOR(S) : Fernand Gobeil, Jr. et al.

It is certified that error appears in the above-identified patent and that said Letters Patent is hereby corrected as shown below:

Column 14, line 25 "—NH—$(CH_2)_{10}$—CO—" should read --...-NH-(CH2)10-CO-...--.

Signed and Sealed this
Nineteenth Day of June, 2012

David J. Kappos
*Director of the United States Patent and Trademark Office*